(12) United States Patent
Lipscomb et al.

(10) Patent No.: US 12,226,731 B2
(45) Date of Patent: Feb. 18, 2025

(54) INFECTIOUS AGENT AIR TREATMENT SYSTEM, APPARATUS, AND METHOD

(71) Applicants: John M. Lipscomb, Cedarburg, WI (US); Edgar C. Paffrath, Cedarburg, WI (US)

(72) Inventors: John M. Lipscomb, Cedarburg, WI (US); Edgar C. Paffrath, Cedarburg, WI (US)

(73) Assignee: G.H.L. International, Inc., Cedarburg, WI (US)

( * ) Notice: Subject to any disclaimer, the term of this patent is extended or adjusted under 35 U.S.C. 154(b) by 343 days.

(21) Appl. No.: 17/519,569

(22) Filed: Nov. 4, 2021

(65) Prior Publication Data

US 2022/0226771 A1    Jul. 21, 2022

Related U.S. Application Data

(60) Provisional application No. 63/075,090, filed on Sep. 4, 2020.

(51) Int. Cl.
   *B01D 53/14*       (2006.01)
   *A41D 13/11*       (2006.01)
   (Continued)

(52) U.S. Cl.
   CPC ...... *B01D 53/1487* (2013.01); *A41D 13/1192* (2013.01); *A61L 9/014* (2013.01); *A61L 2101/20* (2020.08); *B01D 2239/0442* (2013.01)

(58) Field of Classification Search
   CPC ........ B01D 53/1487; B01D 2239/0442; B01D 2252/202; B01D 2257/91; A41D 13/1192;
   (Continued)

(56) References Cited

U.S. PATENT DOCUMENTS 4,319,014 A    3/1982   Peasoe et al.
4,711,793 A    12/1987  Ostreicher et al.
(Continued)

FOREIGN PATENT DOCUMENTS

CN    112641147 A      4/2021
DE    102021000605 A1  5/2021
(Continued)

OTHER PUBLICATIONS

Ott, et al., "Guidance Document for Manufacturing Masks and Respirators for protection against COVID-19," Biorez, Inc., Updated May 21, 2020 (60 pages).
(Continued)

*Primary Examiner* — Frank M Lawrence, Jr.
(74) *Attorney, Agent, or Firm* — Boyle Fredrickson S.C.

(57) ABSTRACT

An air treatment system, e.g., used in a PPE mask, contains media with an infectious agent attenuator that attenuates or inactivates infectious agents in air flowing through passages in a media, the attenuator composed of moisture-activated biocide, e.g., organic acid like citric acid, and a humectant, e.g., gelling humectant like sorbitol, which captures moisture from the air to maintain biocide activation. A surfactant, such as a rhamnolipid surfactant, which attracts and encapsulates infectious agents in the air can be included. The attenuator has a pH≤5, preferably ≤4, more preferably ≤3.5, is kept activated at or below the desired pH by humectant capturing moisture in the breath of a person wearing a mask with the media. A preferred biocide is composed of a solution containing about 88% water and 12% of a mixture that is at least 80% citric acid and no more than 20% sorbitol.

32 Claims, 7 Drawing Sheets

(51) Int. Cl.
*A61L 9/014* (2006.01)
*A61L 9/16* (2006.01)
*A61L 101/20* (2006.01)

(58) Field of Classification Search
CPC ........ A61L 9/014; A61L 2101/20; A61L 9/16; A61L 2209/14; A61L 2209/22; A62B 23/025
USPC ...................................... 55/524; 96/226, 227
See application file for complete search history.

(56) References Cited

U.S. PATENT DOCUMENTS

| | | | |
|---|---|---|---|
| 4,856,509 | A | 8/1989 | Lemelson |
| 5,085,784 | A | 2/1992 | Ostreicher |
| 5,133,878 | A | 7/1992 | Gsell et al. |
| 5,282,971 | A | 2/1994 | Degen et al. |
| 6,780,332 | B2 | 8/2004 | Shiau et al. |
| 2003/0165403 | A1 | 9/2003 | Marsden |
| 2007/0044801 | A1* | 3/2007 | Mathis .................. B32B 5/26 128/206.13 |
| 2008/0317802 | A1 | 12/2008 | Lee et al. |
| 2009/0235933 | A1* | 9/2009 | Wahi .................. D06M 13/17 427/2.3 |
| 2009/0275663 | A1 | 11/2009 | Balekhov et al. |
| 2010/0003166 | A1 | 1/2010 | Park et al. |
| 2010/0034770 | A1 | 2/2010 | Mize |
| 2010/0260645 | A1 | 10/2010 | Low |
| 2010/0282083 | A1 | 11/2010 | Edwards |
| 2010/0330140 | A1 | 12/2010 | Stewarrt et al. |
| 2011/0086118 | A1 | 4/2011 | Kim et al. |
| 2011/0154557 | A1* | 6/2011 | Gray .................. D06M 13/46 2/206 |
| 2012/0060258 | A1 | 3/2012 | Stewart et al. |
| 2012/0234176 | A1 | 9/2012 | Lee |
| 2012/0316305 | A1 | 12/2012 | Bshena et al. |
| 2013/0199375 | A1 | 8/2013 | Wheeler |
| 2015/0021258 | A1 | 1/2015 | Massey et al. |
| 2017/0281993 | A1 | 10/2017 | O et al. |
| 2018/0028952 | A1 | 2/2018 | Peterson, II et al. |
| 2019/0030464 | A1 | 1/2019 | Massey et al. |
| 2020/0217275 | A1 | 7/2020 | Krauss et al. |
| 2021/0386820 | A1 | 12/2021 | Ma et al. |
| 2022/0007754 | A1* | 1/2022 | Kaiserman ............. D06M 11/83 |

FOREIGN PATENT DOCUMENTS

| | | |
|---|---|---|
| WO | 2008014824 A1 | 2/2008 |
| WO | 2020227530 A1 | 11/2020 |

OTHER PUBLICATIONS

2020 VPL Medical Personal Protective Equipment (PPE) Guide.
Zangmeister, et al. "Filtration Efficiencies of Nanoscale Aerosol by Cloth Mask Materials Used to Slow the Spread of SARS-CoV-2." ACS Nano. Jul. 28, 2020;14(7):9188-9200. doi: 10.1021/acsnano.0c05025. Epub Jul. 7, 2020. (13 pages).
Zhou, et al., "Progress and Perspective of Antiviral Protective Material." Adv. Fiber Mater. 2, 123-139 (2020).
Quan, et al., "Universal and reusable virus deactivation system for respiratory protection." Sci Rep 7, 39956 (2017).
Donovan, et al., "Prevention of murine influenza A virus pneumonitis by surfactant nano-emulsions." Antivir Chem Chemother. Jan. 2000;11(1):41-9.

* cited by examiner

Figure 2A Untreated Filter Material

Figure 2B Treated Filter Material

INFECTIOUS AGENT AIR TREATMENT SYSTEM, APPARATUS, AND METHOD

CROSS-REFERENCE TO RELATED APPLICATIONS

This application claims the benefit of U.S. Provisional Applications No. 63/075,090, filed on Sep. 4, 2020, which is incorporated herein by reference in its entirety.

FIELD OF THE INVENTION

The present invention relates generally to an air filter or air filtration system and more particularly to an antiviral air filter or antiviral air filtration system that attenuates and/or inactivates viruses, including coronaviruses, including SARS-COV-2 viruses.

BACKGROUND OF THE INVENTION

Over the past year and a half, an increasing number of people working in the field of epidemiology, including epidemiologists, clinical researchers, clinicians, medical doctors, scientists, engineers and others have made it clear that greater attention must be paid to aerosols as a mode of transmission of the novel coronavirus, aka the SARS-Cov-2 virus, in addition to the larger respiratory droplets already known as a SARS-Cov-2 virus transmission mode. While the size of actual SARS-Cov-2 viruses ranges between a relatively minute 0.06 µm and 0.14 µm, they are known to be found in larger respiratory droplets having a size of at least 5 µm expelled from an infectious person coughing, wheezing, sneezing and even breathing, but have only recently been discovered to be found in smaller aerosols having a size smaller than 5 µm also expelled from an infectious person coughing, wheezing, sneezing and even breathing.

While the difference in size between aerosols and droplets in these two modes of transmission is literally minuscule, acknowledging aerosols as a mode of coronavirus transmission would result in significant changes in how to combat and try to bring an end to the global coronavirus pandemic. In the near term, it would reinforce the clear need for everyone to wear personal protective equipment (PPE), including in the form of surgical masks, N95 respirators, KN95 respirators, to install HEPA room and building air filtration, as well as to continue to engage in social distancing. In the long term, it will require these same people, including engineers, architects, HVAC equipment makers, and HVAC installers to work together to rethink ventilation and air filtration in the design of everything from schools to cruise ships as well as in the retrofitting of HVAC systems of these and other types of buildings and structures to include HEPA filtering in order to try to minimize and preferably prevent the spread of the novel coronavirus via aerosols in the air.

Recent studies have confirmed that floating respiratory aerosols expelled from people infected with the SARS-Cov-2 virus can contain live SARS-Cov-2 viruses and not just fragments of viral genetic material. Live SARS-Cov-2 viruses have been isolated in aerosols at distances ranging from seven feet to as much as sixteen feet from infected hospitalized patients. Other studies have indicated that coronavirus-carrying aerosols can remain airborne for hours and travel distances greater than 40 feet. Such aerosols are typically less than 5 µm in size and can become even smaller while airborne due to evaporation that can occur while they are floating in the air. This has caused a shift from the view that the primary mode of airborne coronavirus transmission was believed to be through larger respiratory droplets having a size typically between 5 µm and 10 µm expelled at considerable velocity from an infected person during a sneeze or cough, it was thought that requiring social distancing by spacing people at least six feet apart would reduce viral transmission because these respiratory droplets are so large and heavy that gravity typically causes them to fall to the ground within four to six feet of the infected person expelling them. Acknowledging these smaller-sized aerosols as another mode of transmission will require even greater steps to be taken than at present to mitigate aerosols as a mode of SARS-Cov-2 virus transmission.

These smaller sized aerosols are of significant concern because they remain airborne much longer than larger respiratory droplets, theoretically can remain airborne indefinitely under many indoor conditions, unless they are removed by or from air currents, dilution with uncontaminated, e.g., outdoor air, ventilation, or via other means. These smaller sized aerosols are also of great concern because it has been found these same size range of particles (i.e., <5 µm) tend to deposit themselves in the more vulnerable lower respiratory tract in humans, as well as has been shown by laboratory testing to do the same in guinea pigs, mice, and monkeys. In contrast, the transmission threat from larger sized respiratory droplets is known to be much less because the spread of larger sized respiratory droplets in the air is typically limited by gravity to only a few feet and such larger sized droplets of between 5-10 µm nearly always only reach the upper airways of the head and neck making their mode of infection less threatening.

What is needed is a better and more efficient way of attenuating or inactivating infectious agents, particularly viruses, more particularly coronaviruses, and even particularly SARS-Cov-2 viruses in both respiratory droplets and especially in airborne aerosols that float in the air inside and throughout buildings and other structures where people work, live or frequently gather. What also is therefore needed is a system, personal protective device and method of attenuating or inactivating viruses, particularly coronaviruses, more particularly SARS-Cov-2 viruses carried by airborne aerosols by infectious agent attenuating or inactivating filter media of such a system, personal protective device and method.

SUMMARY OF THE INVENTION

The present invention is directed to an infectious agent air treatment system configured for treating air in a stream of air flowing therethrough in a manner that disinfects the air by attenuating or inactivating, including by denaturing, airborne infectious agents, including bacteria, viruses, coronaviruses, SARS-Cov-2 viruses, mold, mold spores, fungi and fungi spores, carried in the airstream before a treated airstream exits from the system with any infectious agents in the airstream not filtered out before exiting being attenuated or inactivated. The infectious agent air treatment system is equipped with an infectious agent air treatment stage having an infectious agent attenuating or inactivating air treatment media carrying an infectious agent attenuator that can be coated thereon and/or impregnated therein that includes a biocide, such as preferably an acid-based biocide, more preferably an organic acid that preferably is citric acid, and which is formulated or configured to maintain an infectious agent attenuating or inactivating pH during air flow therethrough that within a desired pH range of between 2-5, preferably a more optimal pH range of between 1-4, and more preferably an optimal or ideal pH range of between 0-3.

A preferred infectious agent attenuator also includes a humectant, which preferably is an organic humectant, such as a humectant which is or includes sorbitol, for preventing inactivation of the biocide by retaining sufficient moisture for keeping the biocide at an optimal pH falling withing an aforementioned desired pH range and preferably within an aforementioned more optimal or ideal pH range that maintains infectious agent attenuation or inactivation efficiency of the infectious agent attenuating or inactivating air treatment media. A preferred infectious agent attenuating or inactivating air treatment media treated with an infectious agent attenuator that includes a humectant that preferably is or includes sorbitol advantageously is configured to be self-activating or at least maintains activation by the humectant capturing moisture in air passing through the infectious agent attenuator coated or impregnated air treatment media during operation helping the attenuator maintain a pH within the aforementioned desired range, preferably within the aforementioned more optimal pH range, and more preferably within the aforementioned ideal pH range.

An embodiment of a treatment media of an infectious agent disinfecting air treatment system of the present invention is equipped with at least one infectious agent inactivating or attenuating air treatment medium that includes, is configured with, and/or adapted as a particulate air filter that filters particulates, including droplets, e.g., respiratory droplets, and particularly aerosols of a size 5 μm and smaller, airborne or entrained in air in the airstream flowing through the at least one infectious agent air treatment medium while also substantially simultaneously attenuating and/or inactivating infectious agents, including viruses, particularly coronaviruses, more particularly SARS-Cov-2 viruses and mutations and variants thereof, which are airborne or entrained in the airstream flowing through the at least one infectious agent air treatment medium. In one such embodiment, the air treatment medium is configured not only to attenuate and/or inactivate infectious agents, including bacteria, viruses, mold, and funguses, but also is configured as an air filter that filters airborne particulates, including bacteria or viruses contained in respiratory droplets and carried by aerosols, as well as filtering out solid particulates, like dust, dander, and the like.

The air treatment media is configured with air flow-through flow passages of relatively small width or diameter formed therein in and/or along an infectious agent attenuating or inactivating attenuator, preferably a moisture carrying an infectious agent attenuating or inactivating attenuator gel, is disposed for ensuring infectious agents in air flowing the infectious agent attenuating or inactivating attenuator containing air treatment media during use and operation contact and are attenuated or inactivated by infectious agent attenuator disposed in and along one or more of these flow paths in and through the air treatment media before exiting the air treatment media. These infectious agent air treating flow paths of the air treatment medium can be defined by at least a plurality of pairs of pores, perforations, dimples, waves, corrugations, passages, channels and/or tubes formed in an infectious agent attenuator containing or carrying air treatment medium and/or which extend substantially completely through the infectious agent attenuator containing or carrying air treatment medium in the general direction of airflow through the treatment media and system during operation and which can have one or more portions thereof extending in one or more different directions relative to the general direction of airflow through the treatment media and system. A plurality or even a plurality of pairs of infectious agent attenuating or inactivating air treatment or air treating flow paths in and/or through the infectious agent treatment media can be and preferably are elongate, non-straight, meandering, crisscrossing, overlapping, generally parallel, disposed alongside one another, arranged in a zig-zagging pattern, or arranged in another pattern, orientation, and/or configuration. These air treatment or air treating flow paths formed in the air treatment media have a relatively small maximum width or maximum diameter of no greater than 0.1 inch, preferably no greater than 10 microns, more preferably no greater than about 1 micron, and even more preferably no greater than 0.1 micron formed therein and/or therethrough distributed throughout every square millimeter of the hard-surfaced air treatment medium, preferably distributed throughout every cubic millimeter of volume of the air treatment media, more preferably distributed substantially uniformly throughout the air treatment media, even more preferably distributed throughout every square millimeter of the air treatment media, and even more preferably substantially uniformly distributed throughout every cubic millimeter of volume of the air treatment media to increase the surface area of infectious agent attenuator disposed along and/or lining each of the flow paths in the air treatment media exposed to air and infectious agents in the air flowing through the air treatment medium during air treatment system operation.

The air treatment media can be made of plastic, e.g., polyethylene and/or polypropylene, composite, or synthetic material; constructed of mesh, wires, fibers, matting, tubes, or the like; and/or be composed of woven or nonwoven material, including woven or nonwoven material, e.g., mesh, made of one or more of plastic, e.g., polyethylene and/or polypropylene, composite, or other synthetic material, such as expanded polytetrafluoroethylene, e.g., expanded polytetrafluoroethylene washable filter membranes, and/or constructed of one or more of mesh, e.g., stainless steel mesh, wires, fibers, matting, tubes, or the like. The above-described airborne infectious agent treating flow paths in the air treatment media are defined by infectious agent attenuator carrying surfaces, coated surfaces or lined surfaces formed of or by structure(s) defining the flow paths, e.g., formed of pores, perforations, dimples, waves, corrugations, passages, channels and/or tubes that define the flow paths, and/or mesh, wires, fibers, matting, tubes, woven material, and/or nonwoven material in at least one layer of air filtration material from which the air treatment media is made or manufactured by impregnating the air filtration material layer with infectious agent attenuator, preferably infectious agent attenuator gel. Prior to infectious agent attenuating or inactivating air treatment system use and operation, infectious agent inactivating or attenuating attenuator is applied in a treatment step to the aforementioned at least one layer of air filtration material to produce infectious agent attenuating or inactivating air treatment media in a manner that coats, adheres, impregnates, clings, absorbs, adsorbs, attaches, affixes or otherwise applies infectious agent attenuator to, on, in, onto and/or into filaments, fibers, fibrils, and other structures of the at least one layer of air filtration material that define the flow paths in the resultant air treatment media produced after application of the infectious agent attenuator.

In a preferred embodiment, the present invention is directed to an infectious agent attenuator carrying, coated and/or impregnated air treatment media configured for use in a personal protective infectious agent inactivating or attenuating air treatment device, which preferably also filters particulates from the air, such as in the form of a surgical mask, N95 respirator, KN95 respirator, N99 respirator, filter mask, or mask filter, and which can be a personal protective air treatment device, which preferably also filters particulates in the air being treated thereby, which is made with an infectious agent attenuator carrying, coated or impregnated air treatment media treated where the infectious agent attenuator is composed of an acid-based biocide along with a humectant and which can be formulated as a gel, such as a hydrogel, containing enough moisture to keep the acid-based biocide moisturized and at a desired pH of less than 5 and preferably less than 3.5 or within a desired pH range of between 0-4 that keeps the biocide activated. The personal protective infectious agent attenuating or inactivating air treatment device, preferably personal protective infectious agent attenuating or inactivating air treatment and filtering device, is configured to be body worn, such as by being configured for being removably mounted to or on a head of a person in a manner that positions the infectious agent attenuator impregnated air treatment media in air flow communication with a mouth and/or nose of the person so infectious agents, including viruses, particularly coronaviruses, more particularly Sars-Cov-2 coronaviruses, in the ambient air, e.g., room air, such as carried by airborne aerosols in the air, inhaled by the person are either attenuated or inactivated by the infectious agent attenuator impregnated air treatment media before entering the person's mouth and/or nose.

The personal air filtering device has a mounting arrangement configured for removably mounting the device onto the head of a person, which can be in the form of a strap, e.g., head strap, band, e.g., adjustable head band, one or more loops, e.g., ear loops, or the like. The personal air filtering device can include a flexible woven structure that structurally supports the infectious agent attenuator impregnated air treatment media as well as any other perforate or porous flow through material, e.g., filter material or filter layers, disposed inline upstream and/or downstream of the infectious agent attenuator impregnated air treatment media. In alternative embodiments, the personal air filtering device can also include one or more valves, such as bypass valves and/or exhaust valves configured to allow air exhaled from a person wearing the personal air filtering device to be exhausted without having to pass through the infectious agent attenuator impregnated air treatment media as well as any other perforate or porous flow through material, e.g., filter material or filter layers, disposed inline with the infectious agent attenuator impregnated air treatment media.

The personal air filtering device preferably has at least one layer of infectious agent attenuator impregnated air treatment media disposed between an ambient air source, e.g., room air, and the mouth and/or nose of a person wearing the device for attenuating or inactivating infectious agents in air being drawn through the air filtering device during inhalation. At least one layer of infectious agent attenuator impregnated air treatment media of the personal air filtering device can be made of a perforate material, such as a perforate mesh filter material, woven filter material, nonwoven filter material, or another type of filter material that can be a hard-surfaced air treatment media material like that disclosed above that is configured not only to receive and carry infectious agent attenuator, but also to filter and trap particulates, aerosols and/or droplets during personal filtering device use and operation. The personal air filtering device can also include one or more additional layers of perforate or porous flow through material not treated or impregnated with infectious agent attenuator disposed in air flow communication with, preferably inline with, and more preferably overlapping at least one layer of the infectious agent attenuator impregnated air treatment media. Where the personal air filtering device is constructed with one or more such additional perforate flow through material layers, each such layer can be composed of an air filtering material, e.g., comprise an air filtering layer, not treated or impregnated with infectious agent attenuator, but which is configured (a) to filter particulates, aerosols, and/or droplets, (b) as a moisture barrier, (c) as a vapor barrier, (d) as an electrostatic filter media, (e) as another type of filter or filter media, and/or (f) as another type of flow-through layer disposed either or both upstream and/or downstream of at least one layer of the infectious agent attenuator impregnated air treatment media. Where one or more such additional layers are present, one or more of the additional layers can be composed or constructed of one or more of the hard-surfaced air treatment media materials of the air treatment system disclosed above.

The infectious agent attenuator impregnated air treatment media is composed of a biocide that preferably is an acid-based biocide at a desired pH, preferably under 5, more preferably under 4, or even more preferably under 3. A preferred acid-based biocide is composed of a carboxylic acid, preferably citric acid, in a strength and pH suitable for disinfecting air coming in contact with such an acid-based acid-containing attenuator by attenuating or inactivating infectious agents in the air including by denaturing the infectious agents. A preferred attenuator is in the form of a liquid or gel, such as a hydrogel, which defines a matrix, a gel matrix or hydrogel matrix, in which the biocide is disposed and which adheres to the air treatment media. In a preferred embodiment, the gel or at least part of the gel is formed of the humectant, which can be a gel forming humectant or gellant, with the gel forming the matrix, e.g., gel matrix or hydrogel matrix, in which the biocide is relatively uniformly, preferably substantially uniformly, distributed.

When such an infectious agent attenuator gel is applied onto the treatment media, the gel coats or lines hard surfaces within the treatment media that define air flow paths therethrough thereby exposing biocide within the gel to infectious agents in the air flowing through the treatment media during personal air filter device use and operation. Where the treatment media is a perforate or porous filter fabric, such as of woven, nonwoven and/or fibrous construction, infectious agent attenuator in a liquid form is applied thereto with the composition of the infectious agent attenuator configured to cause the infectious agent attenuator to gel up upon or after application forming a gel, i.e., infectious agent attenuator gel, which becomes impregnated into the perforate or porous filter fabric.

An infectious agent attenuator impregnated treatment media made with such an infectious agent attenuator formulation, particularly an infectious agent attenuator gel formulation, and a personal protective filter mask having at least one air treatment layer, preferably filter layer, of a treatment media made such an infectious agent attenuator formulation, particularly an infectious agent attenuator gel formulation, is of regenerable construction after being used by application of moisture, e.g., an aqueous regenerating solution, thereto in a manner that wets the infectious agent attenuator, preferably infectious agent attenuator gel, impregnated into the treatment media. Wetting the infectious agent attenuator, preferably infectious agent attenuator gel, impregnated into the treatment media with an aqueous regeneration fluid increases the moisture content of the infectious agent attenuator, preferably infectious agent attenuator gel, thereby regenerating it by the increased moisture content changing its pH. Regenerating the infectious agent attenuator, preferably infectious agent attenuator gel, by remoisturizing it to increase its moisture content after treatment media and/or a personal protective filter mask use advantageously enables the treatment media and personal protective filter mask made with such an attenuator impregnated or attenuator gel impregnated treatment media to be reused over and over again. During regeneration, water in the aqueous regenerating fluid wetting an attenuator gel not only wets and moisturizes biocide in the gel to regenerate the biocide by returning its pH within an aforementioned desired pH range and/or at about a desired pH, but water is absorbed by the gel, preferably absorbed into the gel matrix, that keeps the biocide in the gel moist and within an aforementioned desired pH range and/or at about a desired pH.

In another preferred embodiment and regeneration method where the treatment media is impregnated with an infectious agent attenuator gel, the regeneration fluid preferably is a replenishing fluid containing biocide in an aqueous solution applied onto the infectious agent attenuator gel impregnated treatment media. The applied regeneration fluid wets the treatment media and wets the infectious agent attenuator gel impregnated into the treatment media replenishing the gel impregnated into the treatment media with biocide lost, e.g., via neutralizing reaction, evaporation, sublimation, etc. during treatment media and/or personal protective filter mask use and operation. When wetted by such a biocide-containing aqueous replenishing fluid, water in the fluid advantageously substantially simultaneously regenerates biocide remaining in the gel by moisturizing it, thereby maintaining disinfecting efficiency by keeping it within an aforementioned desired pH range or pH. When wetted by such a biocide-containing aqueous replenishing fluid, biocide in the fluid is advantageously absorbed by the gel and retained within the gel during treatment media and personal protective filter mask use and operation increasing the amount and exposed surface area of biocide available to attenuate or inactivate infectious agents.

The present invention also is directed to an infectious agent attenuating or inactivating personal protective equipment device, such as a surgical mask, multilayer mask or respirator having at least one porous filtering layer impregnated with an infectious agent attenuating or inactivating solution that tries to leave behind an infectious agent attenuating or inactivating attenuator composed of an organic acid that preferably is citric acid, a humectant that preferably is a gelling humectant that preferably is sorbitol which produces or forms a self activating or self replenishing infectious agent attenuator gel and infectious agent attenuating and inactivating air treatment media having a pH of no greater than 5, preferably no greater than 4 and more preferably no greater than 3.5 which is kept moist and activated at or below the desired pH by moisture in the breath of a person wearing the mask. The solution can include a surfactant, such as preferably a rhamnolipid biosurfactant that reduces surface tension both during impregnation of the solution thereby more uniformly impregnating the solution into the at least one porous filtering layer producing an air treatment media having infectious agent attenuating gel more uniformly distributed throughout. The surfactant remains in the gel and reduces surface tension of aerosols and droplets containing viruses and bacteria entrained in the air flowing through the air treatment media contacting the infectious agent attenuating gel more rapidly and efficiently attenuating or inactivating the viruses and bacteria preferably also destroying them by lysing the viruses and bacteria.

DRAWING DESCRIPTION

One or more preferred exemplary embodiments of the invention are illustrated in the accompanying drawings in which like reference numerals represent like parts throughout and in which.

Figure 4:
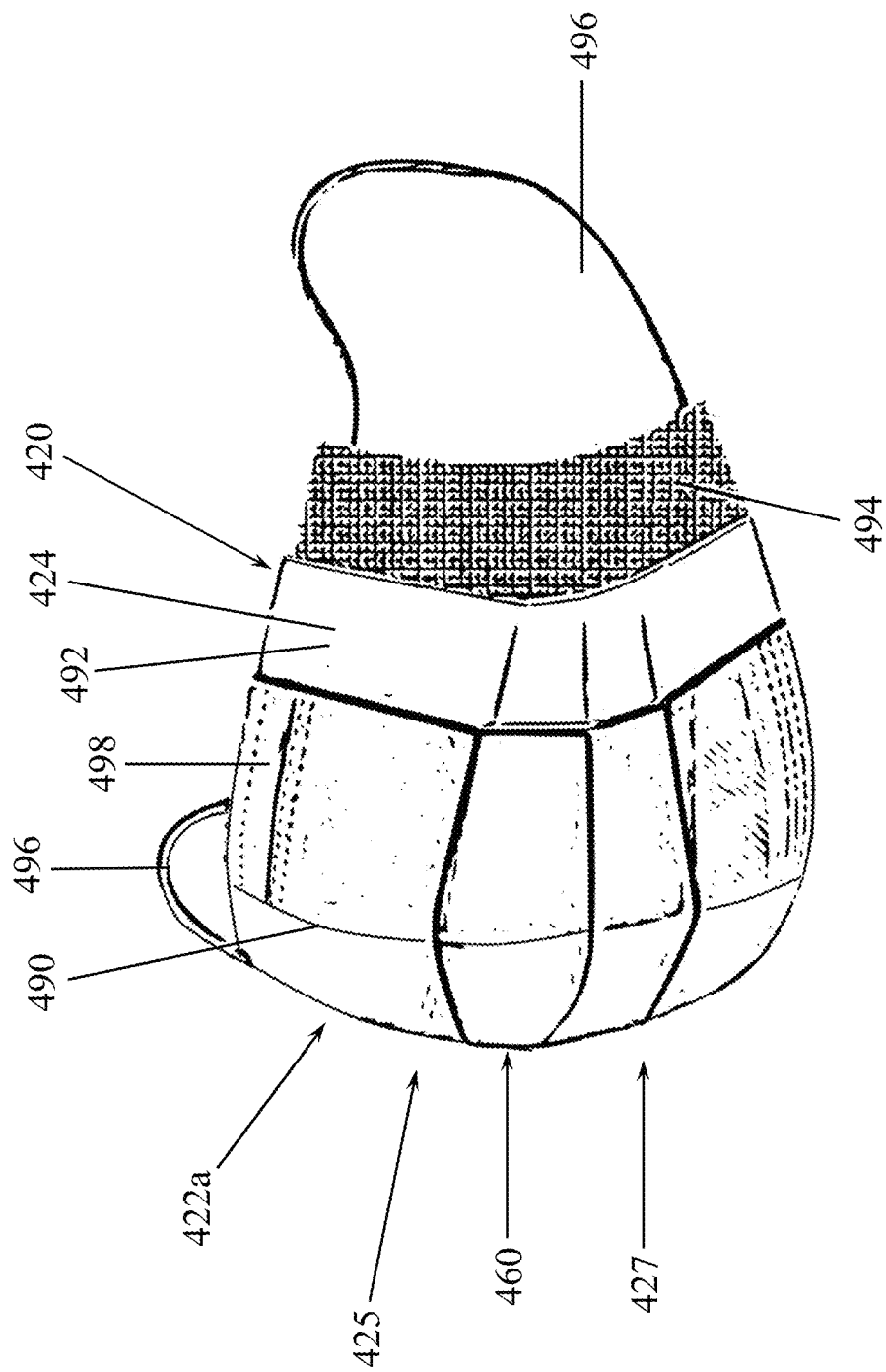
Figure 5:
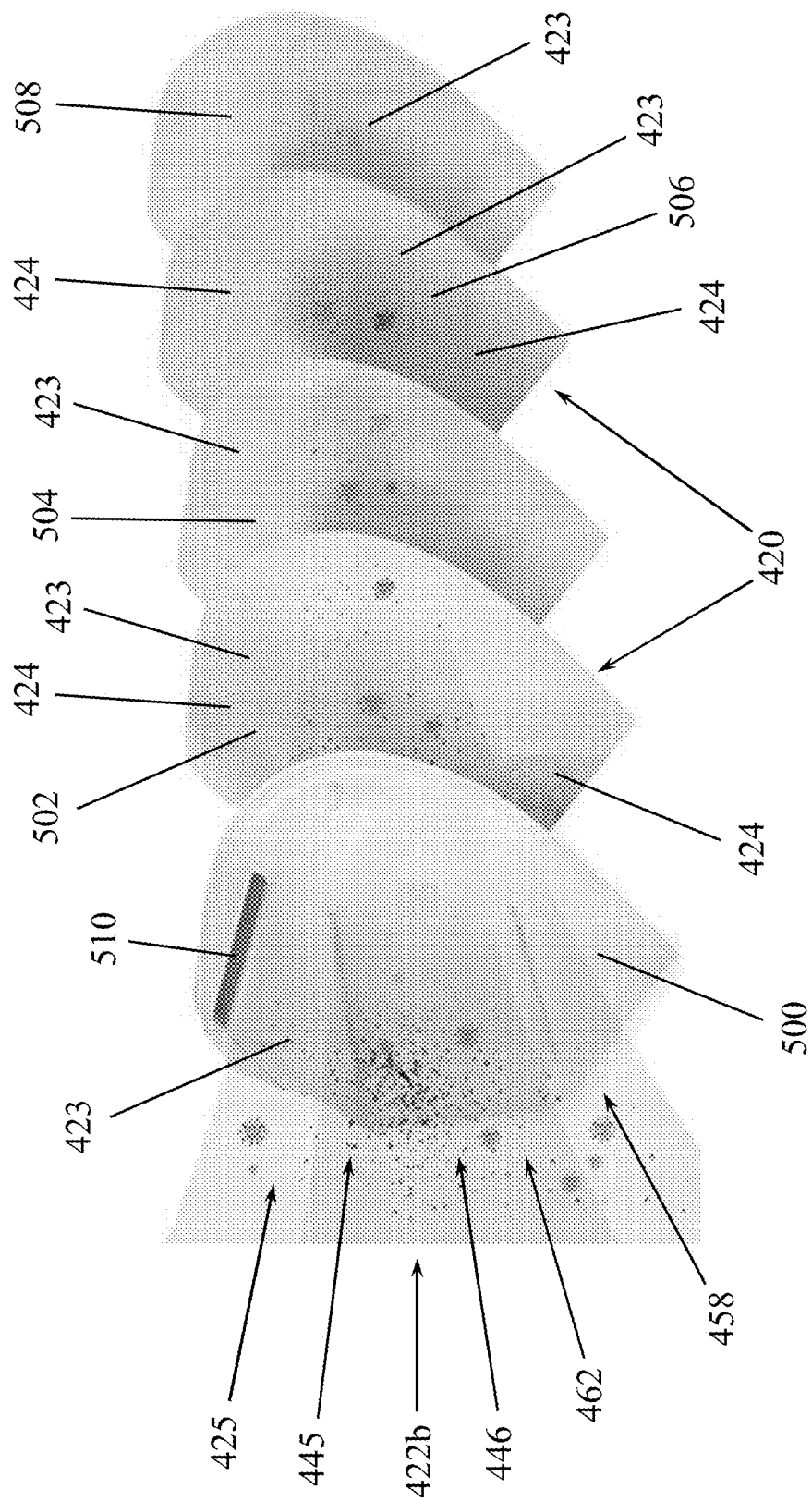
Figure 6:
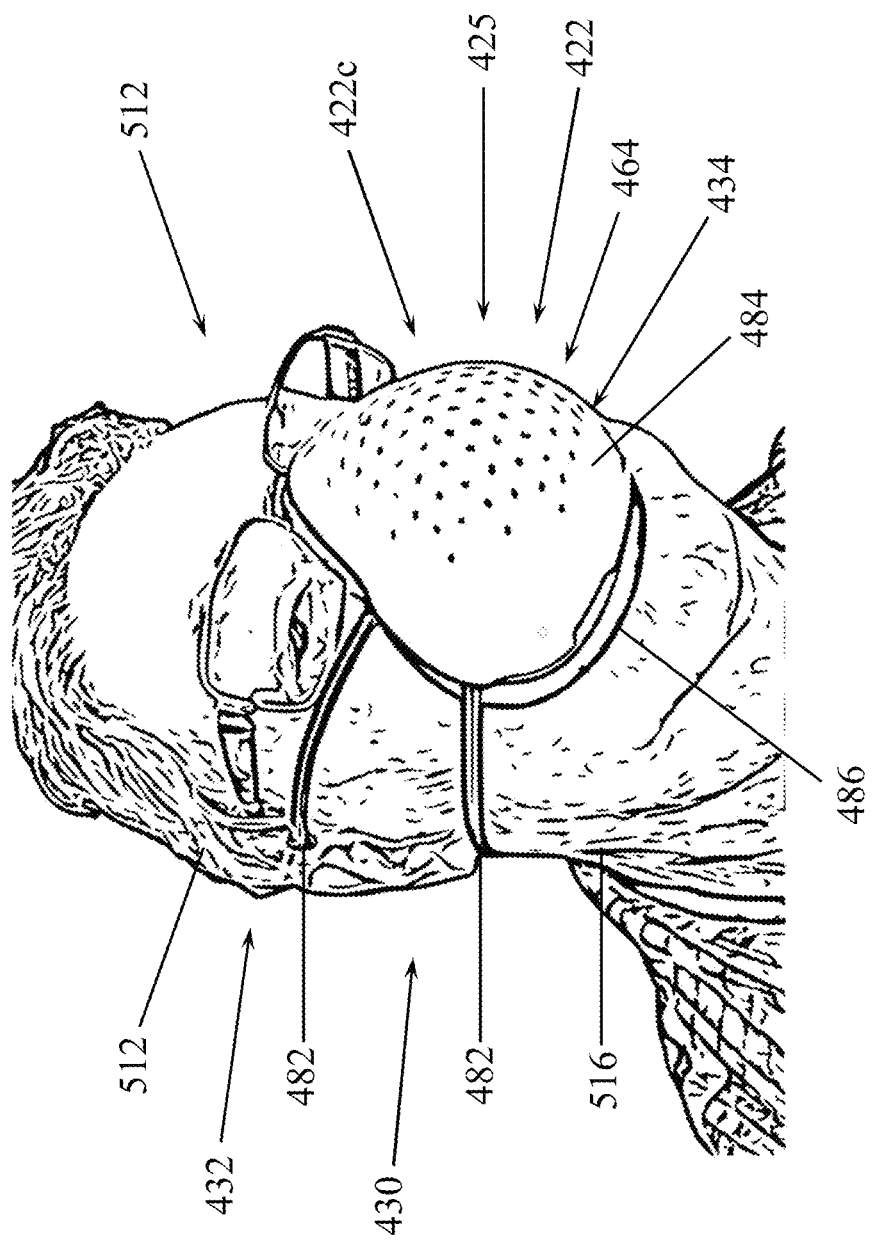
Figure 7:
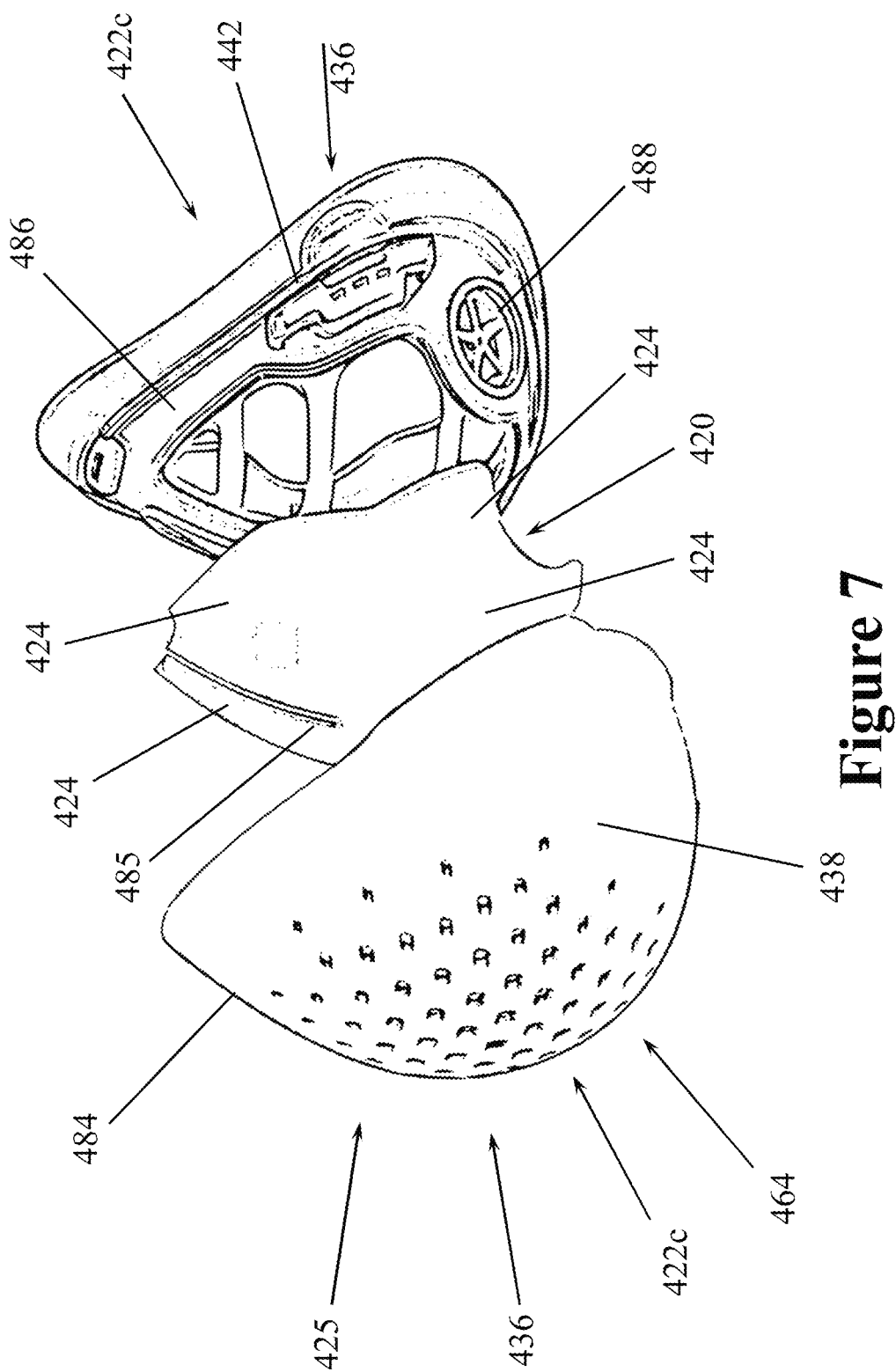

FIG. 4 is a fragmentary perspective cutaway view of a 3-ply or 3-layer infectious agent attenuating or inactivating surgical mask having a first ply or outermost layer composed of a polypropylene spunbound non-woven fabric, a second or middle ply or layer composed of a layer of infectious agent attenuating or inactivating air treatment media made of a perforate or porous air filtering material composed of a meltblown nonwoven fabric impregnated with infectious agent attenuator, and a third ply or innermost layer that is a support layer that composed of a mesh made of a polypropylene spunbound non-woven fabric;

FIG. 5 is a perspective exploded view of the 5-plys or 5-layers of a 5-ply or 5-layer infectious agent attenuating or inactivating air filtering personal protective mask of the present invention that preferably is an N95 respirator mask having a nonwoven first or outer layer made of a fabric like a polypropylene spunbound non-woven fabric, a second outer intermediate double meltblown layer composed of infectious agent attenuating or inactivating air treatment media, a third or middle double nonwoven layer composed of a polypropylene spunbound non-woven fabric, a fourth or inner intermediate double meltblown layer composed of infectious agent attenuating or inactivating air treatment media, and a fifth or inner double nonwoven layer composed of a polypropylene spunbound non-woven fabric;

FIG. 6 is a lower front left perspective view of a person removably wearing a infectious agent attenuating or inactivating respirator assembly of the present invention equipped with a middle layer of air filtering and infectious agent attenuating or inactivating construction composed of infectious agent attenuating or inactivating air treatment media sandwiched between an outer perforate hardshell respirator cover and an inner respirator frame to which ear loops or head anchor straps extend outwardly from; and FIG. 7 is a front top right perspective exploded view of the infectious agent attenuating or inactivating respirator assembly of FIG. 6.

Before explaining one or more embodiments of the invention in detail, it is to be understood that the invention is not limited in its application to the details of construction and the arrangement of the components set forth in the following description and illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

Figure 1:
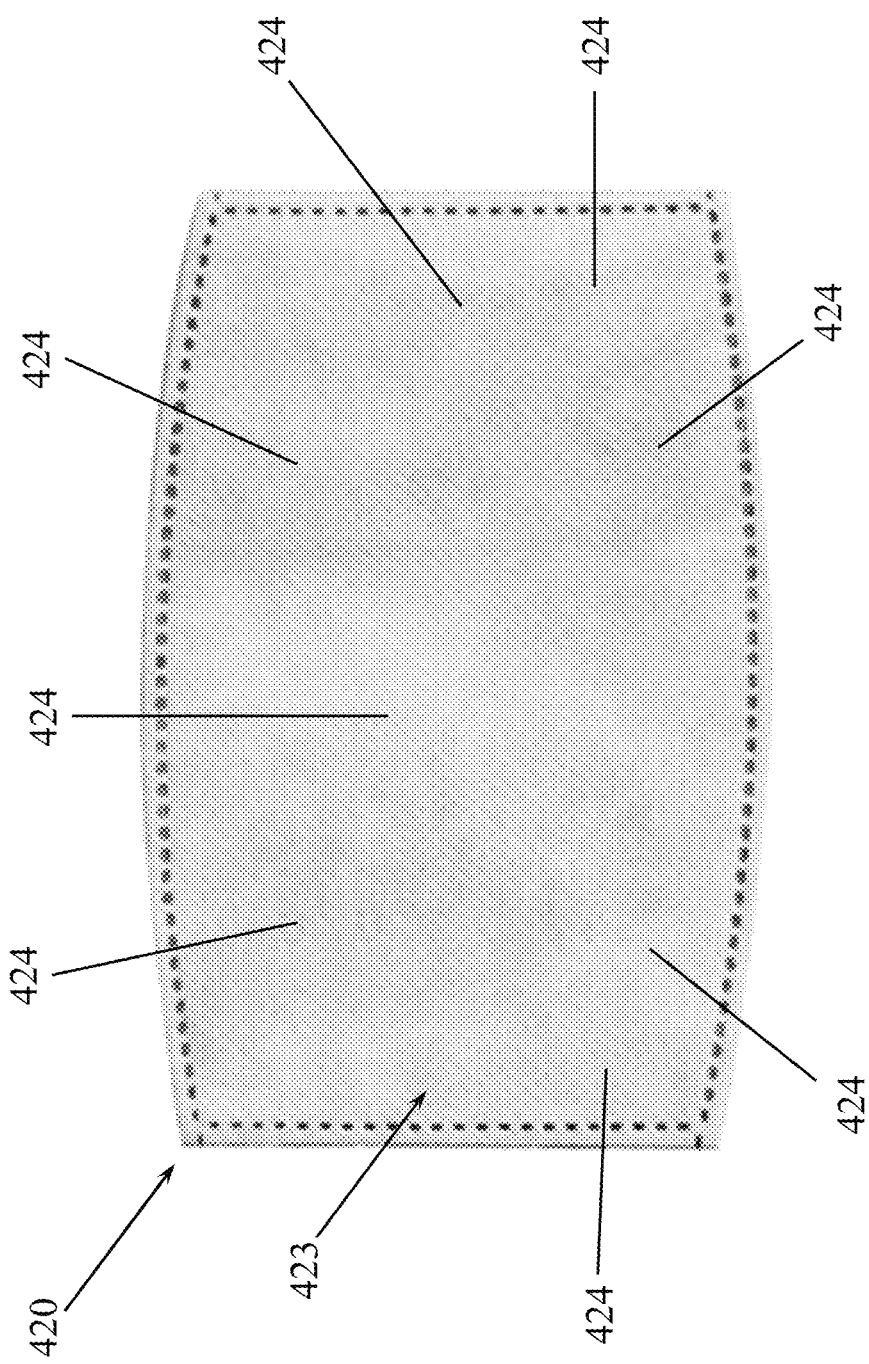
FIG. 1 is a top plan view of an elongate oblong infectious agent attenuating or inactivating air treating filter panel of an infectious agent attenuating or inactivating air treatment media formed of a layer of perforate or porous air filtering material treated with an infectious agent attenuating or inactivating attenuator.

FIG. 1 illustrates a preferred embodiment of an infectious agent attenuating or inactivating air treatment media 420 configured for use in a personal protective air filtering device 422a-422c, such as in the form of a surgical mask 460, like the 3 ply or 3 layer infectious agent attenuating or inactivating surgical mask 460 depicted in FIG. 4, an N-95 or KN-95 air filtering respirator or mask 462, like 5 ply or 5 layer the infectious agent attenuating or inactivating N95 air filtering respirator or mask 462 depicted in FIG. 5, or a hardshell solid frame respirator 464, like the infectious agent attenuating or inactivating respirator 464 equipped with adjustable head and neck straps 482, a perforate concave hardshell outer cover 484 and an cushioned substantially rigid inner frame 486 to which the straps 482 anchor and which has an exhalation valve 488 as depicted in FIGS. 6 and 7, which each employs at least one layer 485 of treatment media 420 made of a perforate or porous air filtering material layer 423 treated, preferably impregnated, with an infectious agent attenuator 424 composed of an infectious agent attenuating or inactivating biocide and a humectant included to retain moisture to keep the biocide activated during use and operation of the personal protective air filtering device 422a-422c. In a preferred embodiment, a sufficient amount of the humectant is added to the infectious agent attenuating or inactivating biocide to produce an infectious agent attenuator 424 of the present invention that is a self-activating infectious agent attenuating or inactivating composition because only moisture in air passing through the air treatment media 420 during inhalation and exhalation by a person wearing the personal protective air filtering device 422 is needed to replenish the infectious agent attenuator 424 of the air treatment media 420 with enough moisture to keep it at a desired pH within an optimal pH range at which the air treatment media 420 attenuates and/or inactivates infectious agents in the air passing through.

Figure 2:
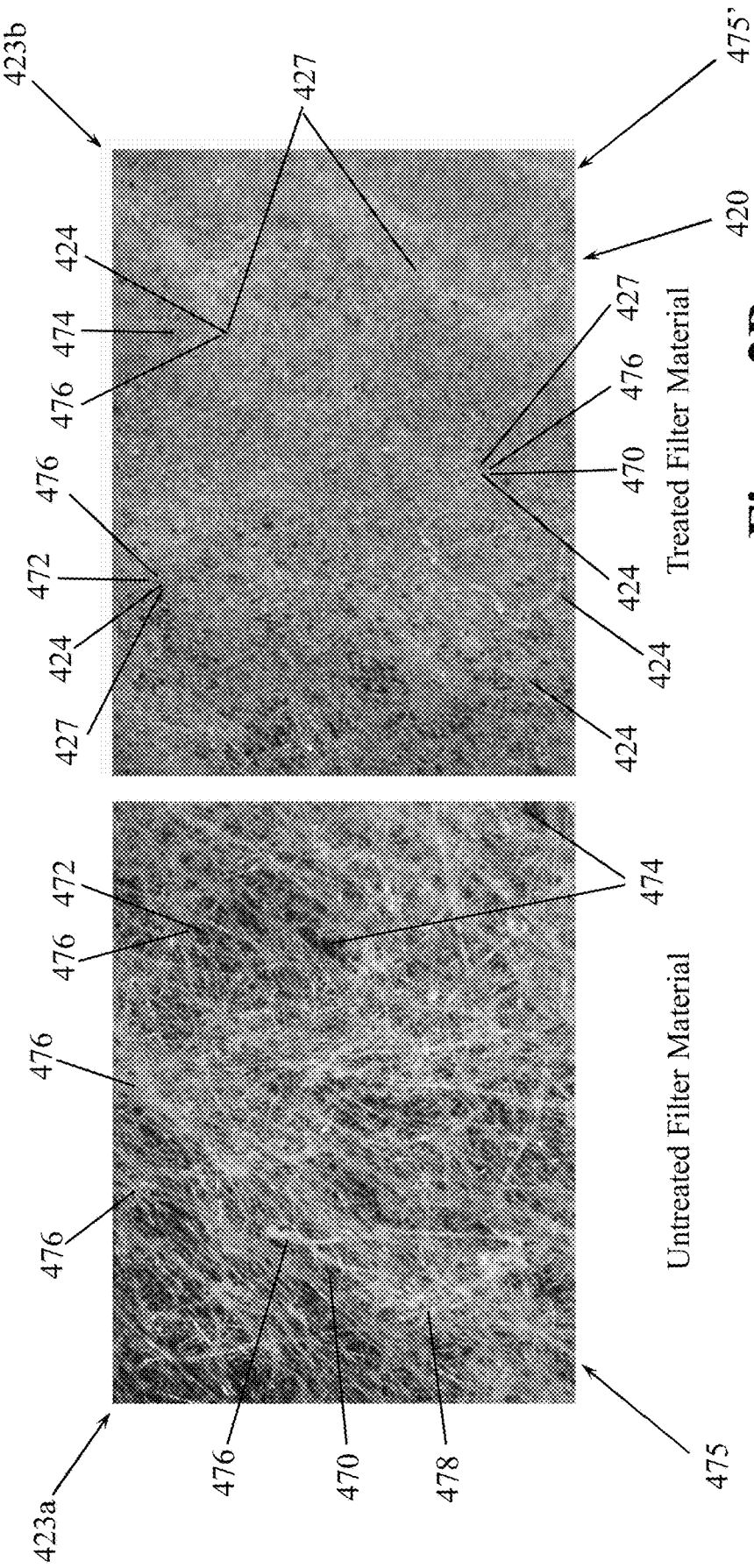
FIGS. 2A and 2B depict a first pair of side by side enlarged photomicrographs of a fragmentary top plan view of an enlarged portion of the oblong layer of perforate or porous air filter material before and after treatment with infectious agent attenuator.
Figure 3:
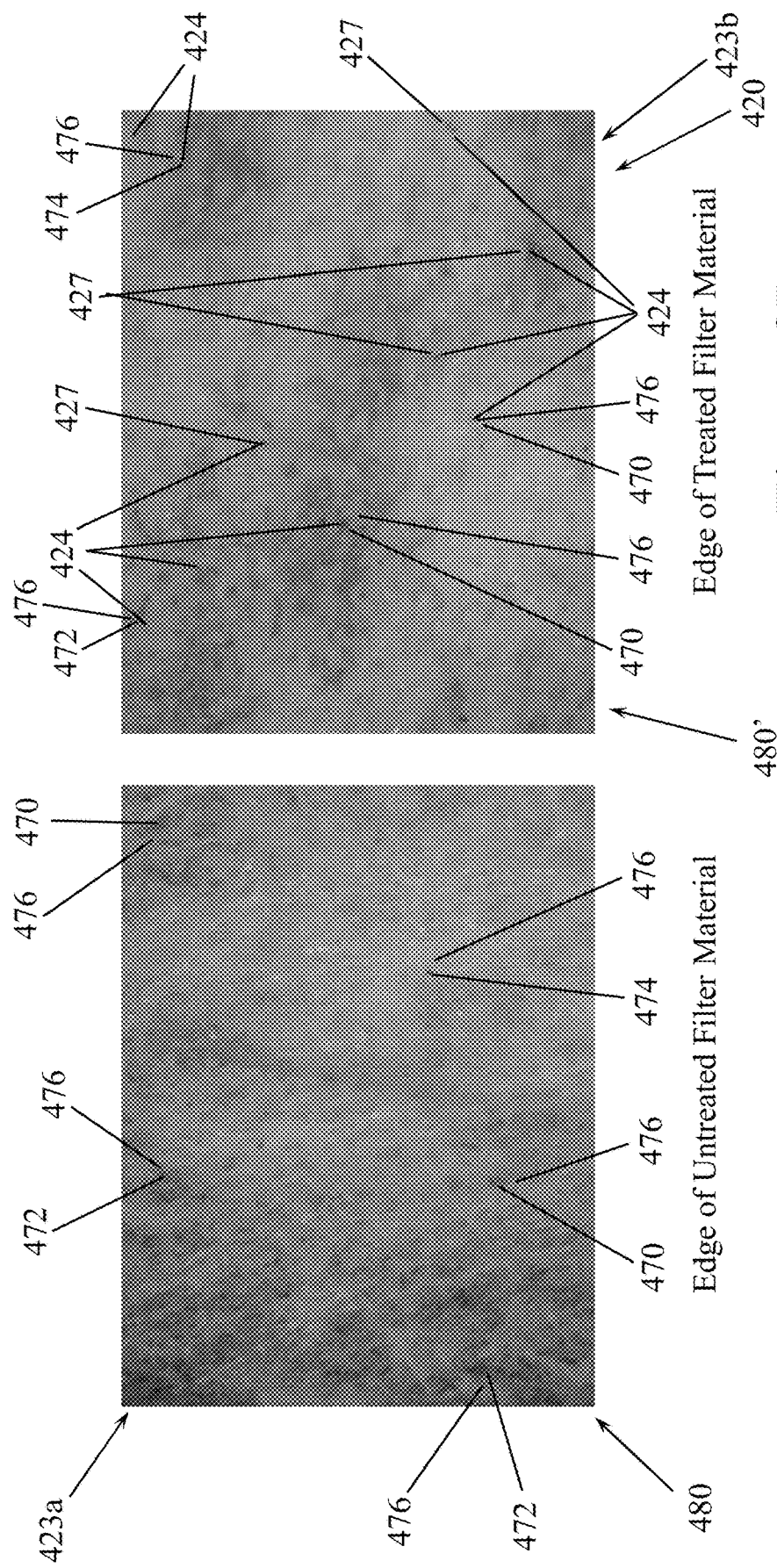
FIGS. 3A and 3B depict a second pair of side by side enlarged photomicrographs of a fragmentary side elevation view of an enlarged portion of a side edge of the oblong layer of perforate or porous air filter material before and after treatment with infectious agent attenuator.

FIGS. 2A and 2B depict a first pair of side by side enlarged photomicrographs of a a top surface 475, 475' of an enlarged portion of the layer of perforate or porous air filter material 423 of FIG. 1 before (FIG. 2A) and after (FIG. 2B) treatment with an infectious agent attenuator 424 that is preferably impregnated therein. FIG. 2A also illustrates that the layer of perforate or porous air filter material 423 has at least a plurality of pairs, i.e. at least 3, of air flow paths or channels 470, 472, 474 which are preferably non-straight or meandering flow paths or channels 470, 472, 474 formed between filaments or fibers 476 of a flexible resilient material 478, such as a material 478 made of a flexible and resilient polypropylene spunbound, meltblown or spunface fabric. It is contemplated that the layer of perforate or porous air filter material can also be made of polyester, cotton, silk or nylon and which can be of woven, nonwoven, knit, meltblown, spunbound or spunface flexible fabric. FIGS. 3A and 3B depict a second pair of side by side enlarged photomicrographs of an enlarged portion of a side edge 480, 480' of the oblong layer of perforate or porous air filter material 423 of FIG. 1 before and after treatment, preferably impregnation, with infectious agent attenuator 424.

FIG. 4 illustrates a 3-ply or 3-layer infectious agent attenuating or inactivating surgical mask 460 having a flexible first ply or outermost layer 490 composed of a polypropylene spunbound non-woven fabric, a flexible second or middle ply or layer 492 composed of a layer of infectious agent attenuating or inactivating air treatment media made of a perforate or porous air filtering material 423 composed of a meltblown nonwoven fabric impregnated with infectious agent attenuator 424, and a flexible third ply or innermost layer 494 that is a support layer composed of a mesh made of a polypropylene spunbound non-woven fabric. The mask also has a pair of elastic ear loops 496 and a bendable metal nose clip 498.

FIG. 5 illustrates a 5-plys or 5-layers of a 5-ply or 5-layer infectious agent attenuating or inactivating air filtering personal protective mask 422b of the present invention that preferably is an N95 respirator mask 462 having a flexible nonwoven concave first or outer layer 500 made of a fabric like a polypropylene spunbound non-woven fabric, a flexible second outer intermediate double meltblown layer 502 composed of infectious agent attenuating or inactivating air treatment media 420, a flexible third or middle double nonwoven layer 504 composed of a polypropylene spunbound non-woven fabric, a flexible fourth or inner intermediate double meltblown layer 506 composed of infectious agent attenuating or inactivating air treatment media 420, and a flexible fifth or inner double nonwoven layer 508 composed of a polypropylene spunbound non-woven fabric. In other words, the 5 ply or 5 layer mask 422b is equipped with a pair of inline but spaced apart infectious agent attenuating or inactivating air treatment media layers 502 and 506 providing double the filtering and infectious agent inactivating or attenuating flow volume. Although equipped with elastic ear loops that are not shown in FIG. 4, the outer layer 500 does have an elongate rectangular bendable metal nose clip 510.

FIGS. 6 and 7 illustrate an infectious agent attenuating or inactivating respirator assembly 464 adapted to be worn over the nose and mouth of a person 512 (FIG. 6). The respirator assembly 464 has a concave middle particulate air filtering layer 485 composed of air filtering and infectious agent attenuating or inactivating media 420 sandwiched between a rigid perforate hardshell outer respirator cover 482 and an inner respirator frame 486 to which adjustable head mounting straps 462 releasably secured around the head 514 and neck 516 of the person 512 wearing the respirator 464 are adjustably anchored.

As can be seen by looking at the comparison views, treating the layer of perforate or porous air filter material 423 with infectious agent attenuator 424 preferably by impregnating the filter material 423 with infectious agent attenuator 424 coats or lines the fibers and/or filaments 476 producing an infectious agent attenuating or inactivating air treatment media 420 configured so infectious agent carrying air flowing through the reduced diameter or width flow paths or channels 470, 472 and 474 comes into contact with the infectious agent attenuator 424 coating or lining the fibers and/or filaments 476. As a result, airborne liquid aerosols and droplets entrained in the flowing air carry infectious agents, such as one or more viruses, e.g., coronaviruses, such as Sars-Cov-2 viruses, which also contact infectious agent attenuator 424 coating or lining the fibers and/or filaments 476 of the air treatment media 420 attenuating or inactivating the infectious agents in the liquid aerosols or droplets.

The infectious agent attenuator 424 preferably is a flowable viscous liquid at room temperature, i.e., 20-22° C. or 68-72° F., during application onto the perforate or porous air filtering material layer 423 such that the attenuator 424 becomes impregnated into the filtering material layer 423 by the liquid or liquified attenuator 424 being distributed substantially completely and preferably substantially uniformly throughout the filtering material layer 423. Upon drying of the attenuator 424 impregnated into the filtering material layer 423, preferably by heated and/or convective oven drying in a heated and/or convective drying oven, the attenuator 424 impregnated into the air filtering material layer 423 solidifies producing an infectious agent attenuating or inactivating air treatment media 420 of the present invention having solidified infectious agent attenuating or inactivating attenuator 424 exposed to air flowing therethrough during personal protective air filtering device operation that is substantially uniformly distributed throughout.

In a preferred embodiment, the flowable liquid infectious agent attenuator 424 is applied to, e.g., impregnated into, the air filtering material layer 423 and is formulated, such as preferably by including a gellant, to increase in viscosity and gel over time during drying producing an infectious agent attenuating or inactivating air treatment media 420 with a moist resilient and pliable infectious agent attenuator gel 427, e.g., preferably indurate gel 427, which will be exposed to air flowing therethrough during personal protective air filtering device operation that congeals substantially uniformly throughout and within the air treatment media 420. The infectious agent attenuator 423 preferably is in the form of a flowable viscous infectious agent attenuator gel 427 that is flowable at room temperature during application to, e.g., impregnating into, the air filtering material layer 423 as a flowable liquid that increases in viscosity and gels as it solidifies after application to the air treatment media 420 as it dries.

A preferred infectious agent attenuator formulation is composed of a biocide and a gellant configured not only to retain water, i.e., a gellant that also is a humectant, to keep the biocide activated, preferably self-activated by human breath moisture during personal protective air filtering device operation, but also to form an infectious agent attenuator gel, preferably during or after application to the air filtering material layer 423 producing an infectious agent attenuating air treatment media 420 of the invention that is ready for use in a personal protective air filtering device 425 like a surgical mask, respirator, or another type of personal protective equipment (PPE). If desired, such a formulation of an infectious agent attenuator 424 can have other constituents including, for example, one or more wetting agents, one or more viscosity modifiers and/or stabilizers, one or more pH modifiers and/or stabilizers, one or more surfactants, e.g., a glycolipid biosurfactant that is a rhamnolipid biosurfactant or supersurfactant, as well as one or more other constituents.

An infectious agent attenuator 424 of the present invention is produced using an infectious agent attenuator solution composed of (a) an infectious agent attenuator precursor mixture composed of between 55-85% of an acid, preferably a tribasic acid or triprotic acid that more preferably is an organic acid, preferably citric acid, and between 15-45% of a humectant that preferably is a gelling humectant, which more preferably is an organic gelling humectant, preferably sorbitol, and (b) the remainder water. The infectious agent attenuator solution used to treat the air filtering material layer 423 to produce the infectious agent attenuating air treatment media 420 with the infectious agent attenuator 424 coated thereon and/or impregnated therein after drying is composed of between 5-20% of the precursor mixture and the remainder, between 80-95%, composed of water into which the concentrated precursor mixture is added and mixed.

A preferred infectious agent attenuator 424 of the present invention is produced using an infectious agent attenuator solution composed of (a) an infectious agent attenuator precursor mixture composed of between 60-80% of a naturally occurring organic acid, preferably citric acid, and between 20-40% of a naturally occurring organic humectant that preferably is a naturally occurring organic gelling humectant, preferably sorbitol, and (b) the remainder composed of water. The infectious agent attenuator solution used to treat the filtering material layer 423 to produce the infectious agent attenuating air treatment media 420 coated and/or impregnated with the infectious agent attenuator 424 is composed of between 10-15% of the precursor mixture and the remainder, between 85-90%, composed of water with which the precursor mixture is added and mixed.

A particularly preferred infectious agent attenuator 424 is produced using an infectious agent attenuator solution having a formulation composed of (a) a precursor mixture of at least 80% of an acid, preferably a naturally occurring organic acid, more preferably citric acid, and no more than 20% of a humectant that preferably is a gelling humectant, more preferably a naturally occurring organic gelling humectant, preferably sorbitol, and (b) water. The infectious agent attenuator solution produced is a flowable liquid solution capable of being applied using a dip-coating application method or being sprayed on using a sprayer or the like that is composed of about 12%±1.5% of the precursor mixture and the remainder, about 88%±1.5%, water mixed together and applied to the air filtering material layer 423 to coat the layer 423 and preferably substantially uniformly impregnate the layer 423 with the solution that solidifies during drying into infectious agent attenuator 424 preferably in the form of an infectious agent attenuator gel 427 transforming the infectious agent attenuator gel-coated and impregnated air filtering material layer 423 into air-filtering infectious agent attenuating treatment media 420.

While a preferred humectant is sorbitol, other humectants, including glycerin, propylene glycol, a longer chain glycol, an acrylic polymer humectant or gellant, and/or calcium chloride can be used. As previously indicated, the infectious agent attenuator solution from which the infectious agent attenuator 424 is produced can be made of a formulation that includes one or more wetting agents, one or more viscosity modifiers and/or stabilizers, one or more pH modifiers and/or stabilizers, one or more surfactants, such as rhamnose lipid(s) surfactants or rhamnolipid biosurfactants, as well as one or more other constituents or components. Where the formulation of the attenuator solution includes one or more of these other components or constituents, the total amount of such one or more of these additional components or constituents makes up no more than 10% of the attenuator solution by solution weight, preferably no more than 5% of the attenuator solution by weight, more preferably no more than about 2.5% of the attenuator solution by weight, at the time of application of the attenuator solution to the air filtering material layer 423 to produce the infectious agent attenuating or inactivating air treatment media 420 containing infectious agent attenuator 424, preferably infectious agent attenuator gel 427, upon suitable drying. Where the formulation of the attenuator solution includes one or more of these other components or constituents, the total amount of such one or more of these additional components or constituents present in the attenuator 424, preferably attenuator gel 427, of the air treatment media 420 makes up no more than 10% of the attenuator 424, preferably attenuator gel 427, by weight, preferably no more than 5% of the attenuator 424, preferably attenuator gel 427, by weight, more preferably no more than about 2.5% of the attenuator 424, preferably attenuator gel 427, by weight.

A preferred formulation of the infectious agent attenuator solution and attenuator 424 may further include a surfactant to facilitate more uniform application of the infectious agent attenuator solution to the air filtering material layer 423 producing an air-filtering infectious agent attenuating treatment media 420 with the attenuator 424, preferably attenuator gel 427, more uniformly distributed throughout the resultant air treatment media 420. In such a preferred infectious agent attenuator solution and attenuator 424 containing a surfactant, the surfactant remains present in the attenuator 424, preferably attenuator gel 427, uniformly distributed throughout the air treatment media 420 and facilitates attenuation or inactivation of infectious agents like viruses such as the SARS-COV2 coronavirus by causing the infectious agents in the air flowing through the media 420 to be more readily attracted to exposed surface of the attenuator 424, preferably attenuator gel 427. In such a preferred infectious agent attenuator solution and attenuator 424 containing a surfactant, the surfactant remains present in the attenuator 424, preferably attenuator gel 427, uniformly distributed throughout the air treatment media 420 and facilitates attenuation or inactivation of infectious agents like viruses such as the SARS-COV2 coronavirus by attracting and encapsulating the infectious agents in the air flowing through the media 420 in the attenuator 424, preferably attenuator gel 427, of the media 420.

Where a surfactant is used, at least one drop of surfactant is added to the infectious agent attenuator solution producing an infectious agent attenuator solution having between 0.001% and 0.1% of surfactant by weight of the solution. In one infectious agent attenuator formulation and solution that made with a surfactant, the solution and the attenuator, including attenuator gel, which results after application and drying of the solution contains between 0.001% and 0.1% of surfactant by weight. In another infectious agent attenuator formulation and solution that contains surfactant, the solution and attenuator that results after application and drying of the solution contains between 0.01% and 1% of surfactant by weight. The inclusion of the surfactant not only reduces surface tension during application, preferably impregnation, by enabling the solution to wick along the fibers and filaments of the filtering material layer 423 more uniformly impregnating the layer 423 therewith producing a more uniform attenuator and gel throughout the resultant air treatment media 420 produced but the surfactant acts on viruses and bacteria in droplets and the like flowing through the media 420 by lysing them destroying the viruses and bacteria contacting the surfactant containing attenuator and attenuator gel lining the air flow passages of the media 420.

In the making of infectious agent attenuating or inactivating air treatment media 420, a filtering material layer 423 can be treated by dipping the filtering material layer 423 into a container of the infectious agent attenuator solution to dip coat the filtering material layer 423 with the solution thereby impregnating the filtering material layer 423 therewith and which is removed from the solution and dried, such as by oven and/or convection drying, to produce an infectious agent attenuating air treatment media 420 of the present invention containing or configured with congealed or solidified infectious agent attenuator 424 exposed to air flowing therethrough that is ready for use in a personal protective air filtering device 422 like a surgical mask, respirator, or another type of personal protective equipment (PPE). The filtering material layer 423 can also be treated by spraying the infectious agent attenuator solution onto the layer 423, such as by using an air spray or air sprayer, a high volume, low pressure (HVLP) spray or sprayer, a low volume, medium pressure (LVMP) spray or sprayer, an airless spray or airless sprayer, an air-assisted airless spray or airless sprayer, or an electrostatic applicator, such as an air spray electrostatic spray or sprayer, an air-assisted airless spray electrostatic spray or sprayer, or rotary atomization electrostatic spray or sprayer, thereby coating and preferably impregnating the layer 423 therewith producing an infectious agent attenuating air treatment media 420 of the present invention containing or configured with congealed or solidified infectious agent attenuator 424 exposed to air flowing therethrough.

When the filtering material layers 423 are treated, the density or thickness of the untreated filtering material 423A increases as compared to the density of the treated filtering material 423b. As seen in FIGS. 1 and 2, when the filtering material layer 423 is treated, the filtering material layer 423 increases in density and minimizes the pores, holes, or airflows within the filtering material 423 through coating the fibers or strands filtering material 423 by increasing the diameter of the fibers. FIG. 1 compares the untreated edge of the filtering material 423a to the treated edge of the filtering material 423b Similarly, FIG. 2 compares the face of the untreated filtering material 423a to the treated filtering material 423b. As seen in FIGS. 1 and 2, the treated filtering material 423b is substantially denser than the untreated filtering material 423a. Thus, the treated filtering material 423b increases the likelihood that infectious agents will contact and adhere to the filtering material 423 and also reduces the likelihood that infectious agents will pass through the filtering material 423 when compared to the untreated filtering material 423a.

A preferred layer of infectious agent attenuating or inactivating filter media 420 has an antiviral efficacy of at least 1.3, preferably at least 1.5, more preferably at least 2.0, when tested for antiviral activity using a human coronavirus in accordance with ISO Test Standard 18184 for a contact time of 10 minutes and showed no bacterial growth of Staphylococcus aureus and Klebsiella pneumonia when the infectious agent attenuating or inactivating filter media 420 was placed in a triptych soy agar or nutrient agar-containing petri dish in accordance with test standard AATCC TM147-2011(2016)e—Test Method for Antibacterial Activity of Textile Materials.

With continued reference to FIGS. 4-7, the present invention is further directed to a personal protective air filtering device 422 made with such an infectious agent attenuator impregnated air treatment media 420 impregnated with infectious agent attenuator 424 composed of acid-based biocide and humectant in an aqueous carrier and which can be formulated as a gel, e.g., a hydrogel, or to form a gel, e.g., hydrogel, which retains enough moisture after application to the treatment media 420 to keep the acid-based biocide moisturized and at or within a desired pH range or pH that keeps the biocide activated and effective. A preferred attenuator formulation is configured as a flowable liquid, e.g., attenuator solution, sprayed onto the treatment media 420, e.g., applied with a spray applicator, dripped onto the treatment media 420, e.g., applied with a spray applicator, misted onto the treatment media 420, e.g., applied with a misting applicator or mister, fogged onto the treatment media 420, e.g., applied with a fogging applicator or fogger, bubbled onto the treatment media 420, e.g., applied with a bubble applicator or bubble generator, and/or applied by dipping the treatment media 420 into a container, e.g., tank or vat, containing the liquid attenuator, e.g., liquid attenuator solution. The applied liquid attenuator is configured or formulated to spread via wetting, wicking and/or capillary action into a hard-surfaced fibrous mesh of the treatment media 420 substantially uniformly distributing attenuator within and throughout the treatment media 420. Such an attenuator is further configured or formulated to increase in viscosity upon or after application to the treatment media 420 until it gels and/or forms a gel that forms an attenuator coating or lining that adheres to the hard surfaces of the mesh of the treatment media 420 thereby impregnating the treatment media 420 with attenuator.

The personal protective air filtering device 422 is a body-worn personal air filtering apparatus 427, preferably a personal air purification filter mask 428, configured to be body worn, by being configured for being removably mounted to or on a head of a person in a manner that positions the infectious agent attenuator impregnated air treatment media 420 in air flow communication with a mouth and/or nose of the person wearing the air treatment device 422 or air filtering apparatus 427 so infectious agents in air flowing through the treatment media 420 are attenuated or inactivated by biocide in attenuator impregnated into the treatment media 420. In a preferred embodiment and method, the personal air filtering device 422 has a mounting arrangement 430 constructed and arranged to removably mount the device 422 onto the head of a person using a head strap, harness, ear loops or another type of mounting arrangement that positions the treatment media 420 adjacent to, inline and preferably overlying the mouth or nose of the person wearing it so inhaled air flows through the treatment media 420 before entering the nose or mouth of the person. In such a preferred embodiment and method, ambient air, such as air in a room or outdoors, flows through the treatment media 420 of the personal air filtering device 422 worn by the person during inhalation by a pressure differential between the ambient air and air in a pocket between the treatment media 420 and mouth of the person created by or during inhalation of the person. In such a preferred embodiment and method, a person wearing the personal air treatment device 422 is the air mover responsible for moving air through the treatment media 420 during inhalation. If desired, the personal air treatment device 422 can be equipped with or otherwise configured with one or more exhalation valves that route exhaled air around the treatment media 420 during exhalation. If desired, the personal air treatment device 422 can be equipped with or otherwise configured with one or more exhalation miniature fans or blowers cause air to flow through the treatment media 420 to the person's mouth and/or nose during use and operation.

The personal air filtering device 422 has a mounting arrangement 430 configured for removably mounting the device 422 onto the head of a person, which can be in the form of a strap, e.g., head strap, band, e.g., adjustable head band, a harness, e.g., adjustable harness, one or more loops, e.g., ear loops, or the like. In the preferred but exemplary air filtering device 422 shown in FIGS. 6 and 7, the mounting arrangement 430 is a head-mounted harness 432 with a plurality of straps 482 and releasable hook-and-loop fastener closure configured to be received and retained around a rear portion of the head, e.g., around a rear portion of the skull, and/or neck of a person wearing the device 422. The mounting arrangement 430, e.g., harness 432, can be of an adjustable configuration and/or elastic construction to enable location and fitment of an air treatment media carrier 434 in air flow communication with the nose and/or mouth of a person wearing the device 422.

The air treatment media carrier 434 is configured to carry the infectious agent attenuator impregnated air treatment media 420 and locate the treatment media 420 so the treatment media 420 is generally inline with, overlies and is disposed in air flow communication with the nose and/or mouth of a person wearing the air treatment device 422 during air disinfecting use and operation of the device 422. In the embodiment shown in FIG. 5, the air treatment media carrier 434 includes an infectious agent attenuator impregnated air treatment media structural support assembly 436, such as in the form of a concave housing 438, e.g., perforate concave outer plastic shell 440, which mates with a concave perforate structural support frame 442 equipped with a inner peripheral face seal 445 and carries and/or structurally supports the infectious agent attenuator impregnated air treatment media 420 therebetween. Where of multilayer construction, the air treatment media structural support assembly 436 also supports any other perforate or porous flow through material, e.g., filter material or filter layers, e.g., additional layer(s), disposed inline upstream and/or downstream of the air treatment media 420. Where of multilayer construction, the air treatment media 420 and layer(s) of filter media are removably captured between the outer housing 438 and inner support frame 442. The personal air filtering device 422 can also include one or more valves 447, such as bypass valves and/or exhaust valves configured to allow air exhaled from a person wearing the personal air filtering device 422 to be exhausted and can be configured to do so without having to pass back through the treatment media 420 as well as having to flow through any other perforate or porous flow through material, e.g., filter material or filter layers, disposed inline with the treatment media 420 during exhalation.

The personal air filtering device 422 has at least one layer of infectious agent attenuator impregnated air treatment media 420 disposed between an ambient air source, e.g., room air, and the mouth and/or nose of a person wearing the device 422 for attenuating or inactivating infectious agents in air being drawn through the device 422 during inhalation by the person. The treatment media 420 of the personal air filtering device 422 is made of a perforate material, such as a perforate mesh material, woven material, nonwoven material, or another type of perforate and/or porous material that can be a hard-surfaced air treatment media material like that disclosed above with regards to the treatment media embodiments. Such a perforate air treatment media material can be a woven material, nonwoven material, or other type of perforate and/or porous material, which can be and preferably is of water-impervious construction, e.g., made of a perforate or porous material impervious to water. Such a perforate or porous air treatment media material, woven material, nonwoven material, or another type of perforate and/or porous material can be and preferably also is of reusable and/or washable construction, e.g., made of a washable material and/or a reusable material. Such a material can be a melt-blown material, a spunbound material, cotton, or another type of woven or nonwoven porous and/or perforate material.

With reference once again to FIG. 5, the treatment media 422 can be used in a multilayer filter mask 445, such as a multilayer surgical mask or more preferably an N-95, N-99, KN-95 or KN-99 respirator 446 having a perforate air filtering and treatment assembly 458 with at least a plurality of pairs of perforate, porous or flow-through layers 500, 502, 504, 506 and/or 508 with at least one of the layers being a particulate filter layer, preferably a plurality of the layers being particulate filtering layers, and at least one of the layers that is or composed of an infectious agent attenuator impregnated air treatment media 420. In an exemplary embodiment, the air filtering and treatment assembly 458 has at least one inner layer 452 that is an infectious agent attenuator impregnated air treatment media 420 sandwiched between at least a pair of air filter layers and preferably sandwiched between a plurality of pairs of air filter layers 500, 504 and 504, 508, such as is depicted in FIG. 5. Any of the layers can be made of any of the filter materials and/or air treatment media materials discussed elsewhere herein.

In at least one embodiment, the filter media 420, preferably at least one layer of filter media 420, where of multilayer construction, is made of such a perforate material, preferably perforate mesh material, configured not only to receive and carry infectious agent attenuator, but also or includes a perforate particulate filter material configured to filter and trap particulates, aerosols and/or droplets during personal filtering device use and operation. The personal air filtering device 422 can also include one or more additional layers of perforate or porous flow through material not treated or impregnated with infectious agent attenuator disposed in air flow communication with, preferably inline with, and more preferably overlapping at least one layer of the infectious agent attenuator impregnated air treatment media.

Where the personal air filtering device 422 is constructed with one or more such additional perforate flow through material layers not carrying or being impregnated with infectious agent attenuator, each such layer can be composed of an air filtering material, e.g., comprise an air filtering layer, not treated or impregnated with infectious agent attenuator, but which is configured (a) to filter particulates, aerosols, and/or droplets, (b) as a moisture barrier, (c) as a vapor barrier, (d) as an electrostatic filter media, (e) as another type of filter or filter media, and/or (f) as another type of flow-through layer disposed either or both upstream and/or downstream of at least one layer of the infectious agent attenuator impregnated air treatment media. Where one or more such additional layers are present, one or more of the additional layers can be composed or constructed of one or more of the hard-surfaced air treatment media materials of the air treatment system disclosed above but not containing, treated with nor impregnated with attenuator 424.

A preferred infectious agent attenuator used in the infectious agent attenuator impregnated air treatment media 420 is composed of a biocide that preferably is an acid-based biocide in combination with a humectant configured to retain moisture, e.g., water, to keep the biocide moisturized and at a desired pH, preferably no more than about 3 pH, or within a suitable pH range of between 0 and 5 pH, preferably between 0-4 pH, and more preferably between 0-3 pH. A preferred acid-based biocide is composed of a carboxylic acid, preferably citric acid, in a strength and pH suitable for disinfecting air coming in contact with such an acid-based or acid-containing attenuator by attenuating or inactivating infectious agents in the air including by denaturing the infectious agents. A preferred attenuator is in the form of a gel, such as a hydrogel, which defines a matrix, a gel matrix or hydrogel matrix, in which one or both the biocide and humectant are disposed and which adheres to the air treatment media. In a preferred embodiment, the gel or at least part of the gel is formed of the humectant, which can be a gel forming humectant or gellant, with the gel forming the matrix, e.g., gel matrix or hydrogel matrix, in which the biocide is relatively uniformly, preferably substantially uniformly, distributed.

When such an infectious agent attenuator gel is applied onto the treatment media 420, the gel coats or lines hard surfaces within the treatment media that define air flow paths therethrough thereby exposing biocide within the gel to infectious agents in the air flowing through the treatment media 420 during personal air filter device use and operation. Where the treatment media 420 is a perforate or porous filter fabric, such as of woven, nonwoven and/or fibrous construction, infectious agent attenuator in a liquid form is applied thereto with the composition of the infectious agent attenuator configured to cause the infectious agent attenuator to gel up upon or after application forming a gel, i.e., infectious agent attenuator gel, which becomes impregnated into the perforate or porous filter material of the filter media 420.

An infectious agent attenuator impregnated treatment media 420 made with such an infectious agent attenuator formulation, particularly an infectious agent attenuator gel formulation, and a personal protective filter device 422 having at least one infectious agent attenuating air treatment layer, preferably filter layer, of a treatment media 422 made of such an infectious agent attenuator formulation, particularly an infectious agent attenuator gel formulation, is of regenerable construction after being used for a period of time by application thereto of a regenerating fluid that preferably is an aqueous liquid regenerating solution. Such an aqueous liquid regenerating solution contains water and wets the infectious agent attenuator, preferably infectious agent attenuator gel, impregnated into the treatment media 420 when the aqueous liquid regenerating solution is applied to the treatment media 420. Wetting the infectious agent attenuator, preferably infectious agent attenuator gel, impregnated into the treatment media 420 with an aqueous regeneration fluid increases the moisture content of the infectious agent attenuator, preferably infectious agent attenuator gel, thereby regenerating it by the increased moisture content changing its pH, preferably increasing its pH, so its pH is within a range of between 4 and 7 pH, preferably between about 5 and 6 pH, and more preferably about 5.5 pH. Regenerating the infectious agent attenuator, preferably infectious agent attenuator gel, by remoisturizing it to increase its moisture content after treatment media and/or a personal protective filter device use advantageously enables the treatment media 420 and personal protective filter device 422, 422' made with such an attenuator impregnated or attenuator gel impregnated treatment media 420 to be reused over and over again. In other words, a regeneration cycle or regeneration can be performed at least a plurality of pairs of, i.e., at least three, times to regenerate the treatment media 420 of the device 422 at least a plurality of pairs of, i.e., at least three, times. During regeneration, water in the aqueous regenerating fluid wetting an attenuator gel not only wets and moisturizes biocide in the gel to regenerate the biocide by returning its pH within an aforementioned desired pH range and/or at about a desired pH, but water is absorbed by the gel, preferably absorbed into the gel matrix, that keeps the biocide in the gel moist and within an aforementioned desired pH range and/or at about a desired pH. In one preferred formulation, the aqueous regenerating fluid is a liquid composed substantially completely of water.

In another preferred embodiment and regeneration method where the treatment media 420 is impregnated with an infectious agent attenuator gel, the regeneration fluid preferably is a replenishing fluid containing biocide in an aqueous solution applied onto the infectious agent attenuator gel impregnated treatment media.

The applied regeneration fluid wets the treatment media and wets the infectious agent attenuator gel impregnated into the treatment media replenishing the gel impregnated into the treatment media with biocide lost, e.g., via neutralizing reaction, evaporation, sublimation, etc. during treatment media and/or personal protective filter mask use and operation. When wetted by such a biocide-containing aqueous replenishing fluid, water in the fluid advantageously substantially simultaneously regenerates biocide remaining in the gel by moisturizing it, thereby maintaining disinfecting efficiency by keeping it within an aforementioned desired pH range or pH. When wetted by such a biocide-containing aqueous replenishing fluid, biocide in the fluid is advantageously absorbed by the gel and retained within the gel during treatment media and personal protective filter mask use and operation increasing the amount and exposed surface area of biocide available to attenuate or inactivate infectious agents.

A preferred air breath moisture activated and regenerated infectious agent attenuating mask of the present invention has an air filtering layer of the mask that is or includes a layer of infectious agent attenuating or inactivating filter media 420 with an antiviral efficacy of at least 1.3, preferably at least 1.5, more preferably at least 2.0, when tested for antiviral activity using a human coronavirus in accordance with ISO testing standard 18184 for a contact time of 10 minutes and showed no bacterial growth of Staphylococcus aureus and Klebsiella pneumonia when infectious agent attenuating or inactivating filter media 420 was placed in a triptych soy agar or nutrient agar —containing petri dish in accordance with test standard AATCC TM147-2011(2016) e—Test Method for Antibacterial Activity of Textile Materials.

In a preferred embodiment, the personal air filtering device 422 is a three-layer, four-layer or five layer surgical mask having at least one layer composed of an infectious agent attenuator impregnated air treatment media made in accordance with the following specifications:

Hypoallergenic Safe & Comfort
3 extra thick ply with ear loops
Bacterial Filtration Efficiency or B.F.E>95%
Particle Filtration Efficiency or P.F.E>95%
Manufactured under ISO 9001 and/or meets ISO 9001
Has a water repellent top/outer & base/inner layer
Made with layers of Fiberglass-free filter medium
Outer layer—Hydrophobic non-woven layer
Middle layer—Meltblown filter
Inner layer—Soft absorbent layer
Adjustable nose bridge

| Characteristic | N95 |
| --- | --- |
| Bacterial filtration efficiency | ≥95% |
| Sub-micron particulates filtration efficient at 0.3 micron | ≥95% |
| Differential pressure, mm H20/cm2 (Breathability) | <5.0 |
| Resistance to penetration by synthetic blood, the minimum pressure in mm Hg for pass result | 160 mm Hg |

The present invention also is directed to an infectious agent attenuating or inactivating personal protective equipment device, such as a surgical mask, multilayer mask or respirator having at least one porous filtering layer impregnated with an infectious agent attenuating or inactivating solution that tries to leave behind an infectious agent attenuating or inactivating attenuator composed of an organic acid that preferably is citric acid, a humectant that preferably is a gelling humectant that preferably is sorbitol which produces or forms a self activating or self replenishing infectious agent attenuator gel and infectious agent attenuating and inactivating air treatment media having a pH of no greater than 5, preferably no greater than 4 and more preferably no greater than 3.5 which is kept moist and activated at or below the desired pH by moisture in the breath of a person wearing the mask. The solution can include a surfactant, such as preferably a rhamnolipid biosurfactant that reduces surface tension both during impregnation of the solution thereby more uniformly impregnating the solution into the at least one porous filtering layer producing an air treatment media having infectious agent attenuating gel more uniformly distributed throughout. The surfactant remains in the gel and reduces surface tension of aerosols and droplets containing viruses and bacteria entrained in the air flowing through the air treatment media contacting the infectious agent attenuating gel more rapidly and efficiently attenuating or inactivating the viruses and bacteria preferably with the reduced surface tension produced by the inclusion of the surfactant also destroying them by lysing the viruses and bacteria.

Understandably, the present invention has been described above in terms of one or more preferred embodiments and methods. It is recognized that various alternatives and modifications may be made to these embodiments and methods which are within the scope of the present invention.

What is claimed is:

1. An air treatment system comprised of an air treatment media having at least a plurality of pairs of air flow passages formed therein and an infectious agent attenuator configured to attenuate or inactivate infectious agents in the air flowing through the air flow passages in the air treatment media, the infectious agent attenuator comprised of:
   (a) a moisture-activated infectious agent attenuating or inactivating biocide, and
   (b) a humectant comprised of sorbitol, the humectant capturing moisture from the air flowing through the air flow passages in the air treatment media, the captured moisture maintaining the attenuating or inactivating effectiveness of the infectious agent attenuator by maintaining moisture activation of the infectious agent attenuating or inactivating biocide.

2. The air treatment system of claim 1, wherein the moisture-activated infectious agent attenuating or inactivating biocide is comprised of an acid.

3. The air treatment system of claim 1, wherein the infectious agent attenuator is further comprised of a surfactant, the surfactant configuring the infectious agent attenuator to attract and encapsulate infectious agents in the air flowing through the air flow passages in the air treatment media.

4. The air treatment system of claim 3, wherein the surfactant is comprised of a glycolipid surfactant.

5. The air treatment system of claim 1, wherein the infectious agent attenuator is further comprised of a surfactant configured to attract and encapsulate the infectious agent attenuator infectious agents in the air flowing through the air flow passages in the air treatment media.

6. The air treatment system of claim 5, wherein the surfactant is comprised of a biosurfactant.

7. The air treatment system of claim 2, wherein the moisture-activated infectious agent attenuating or inactivating biocide is comprised of an organic acid.

8. The air treatment system of claim 1, wherein the infectious agent attenuator is composed of a solution comprised of (a) about 88% water by solution weight, and (b) about 12% by solution weight of a mixture comprised of (i) at least 80% infectious agent attenuating or inactivating biocide by mixture weight, and (ii) no more than 20% sorbitol by mixture weight.

9. The air treatment system of claim 1, wherein the moisture-activated infectious agent attenuating or inactivating biocide is comprised of an acid, and the infectious agent attenuator is composed of a solution comprised of (a) about 88% water by solution weight, and (b) about 12% by solution weight of a mixture comprised (i) of at least 80% acid by mixture weight, and (i) no more than 20% sorbitol by mixture weight.

10. The air treatment system of claim 9, wherein the moisture-activated infectious agent attenuating or inactivating biocide is comprised of citric acid.

11. The air treatment system of claim 1, wherein the humectant maintains a pH of the infectious agent attenuating or inactivating biocide that is no greater than 5.

12. The air treatment system of claim 1, wherein the infectious agent attenuator is composed of a solution comprised of (a) between 80% and 95% water by solution weight, and (b) between 5% and 20% by solution weight of a mixture comprised of (i) between 55% and 85% infectious agent attenuating or inactivating biocide by mixture weight, and (ii) between 15% and 45% sorbitol by mixture weight.

13. The air treatment system of claim 12, further comprising between 0.001% and 0.1% of a surfactant.

14. The air treatment system of claim 4, wherein the surfactant comprises a rhamnolipid surfactant.

15. The air treatment system of claim 6, wherein the surfactant comprises a rhamnolipid surfactant.

16. An air treatment system comprised of an air treatment media having at least a plurality of pairs of air flow passages formed therein and extending therethrough, and an infectious agent attenuator configured to attenuate or inactivate infectious agents in air flowing through the air flow passages in the air treatment media, the infectious agent attenuator comprised of:
  (a) an infectious agent attenuating or inactivating biocide, and
  (b) a humectant comprised of sorbitol, the humectant capturing moisture from the air flowing through the air flow passages in the air treatment media, the captured moisture maintaining infectious agent attenuation and inactivation effectiveness by maintaining a pH thereof which is (i) no greater than a predetermined pH, or (ii) within a predetermined pH range that maintains infectious agent attenuation or inactivation effectiveness of the infectious agent attenuator.

17. The air treatment system of claim 16, wherein the moisture-activated infectious agent attenuating or inactivating biocide is comprised of an acid.

18. The air treatment system of claim 17, wherein the infectious agent attenuator is further comprised of a surfactant that facilitates attraction of infectious agents in the air flowing through the air flow passages increasing infectious agent attenuation or inactivation effectiveness.

19. The air treatment system of claim 18, wherein the surfactant is comprised of a glycolipid surfactant.

20. The air treatment system of claim 17, wherein the infectious agent attenuator is further comprised of a surfactant, the surfactant configuring the infectious agent attenuator to attract and encapsulate infectious agents in the air flowing through the air flow passages.

21. The air treatment system of claim 20, wherein the surfactant is comprised of a biosurfactant.

22. The air treatment system of claim 17, wherein the infectious agent attenuating or inactivating biocide is comprised of citric acid.

23. The air treatment system of claim 16, wherein the infectious agent attenuator is composed of a solution comprised of (a) about 88% water by solution weight, and (b) about 12% by solution weight of a mixture comprised of (i) at least 80% infectious agent attenuating or inactivating biocide by mixture weight, and (ii) no more than 20% sorbitol by mixture weight.

24. The air treatment system of claim 16, wherein the infectious agent attenuating or inactivating biocide is comprised of an acid, and the infectious agent attenuator is composed of a solution comprised of (a) about 88% water by solution weight, and (b) about 12% by solution weight of a mixture comprised of (i) at least 80% acid by mixture weight, and (ii) no more than 20% sorbitol by mixture weight.

25. The air treatment system of claim 16, wherein the infectious agent attenuator is composed of a solution comprised of (a) between 80% and 95% water by solution weight, and (b) between 5% and 20% by solution weight of a mixture comprised of (i) between 55% and 85% infectious agent attenuating or inactivating biocide by mixture weight, and (ii) between 15% and 45% sorbitol by mixture weight.

26. The air treatment system of claim 25, further comprising between 0.001% and 0.1% of a surfactant.

27. The air treatment system of claim 26, wherein the surfactant comprises a glycolipid surfactant.

28. The air treatment system of claim 27, wherein the surfactant comprises a rhamnolipid surfactant.

29. The air treatment system of claim 25, wherein the infectious agent attenuating or inactivating biocide is comprised of an organic acid.

30. The air treatment system of claim 29, wherein the infectious agent attenuating or inactivating biocide is comprised of citric acid.

31. The air treatment system of claim 19, wherein the surfactant comprises a rhamnolipid surfactant.

32. The air treatment system of claim 16, wherein the humectant maintains the pH of the infectious agent attenuating or inactivating biocide that is no greater than 5.

* * * * *